US009533939B2

(12) United States Patent
Mitchell et al.

(10) Patent No.: US 9,533,939 B2
(45) Date of Patent: Jan. 3, 2017

(54) PROCESS FOR THE CONVERSION OF AROMATIC NITRO COMPOUND INTO AMINES

(75) Inventors: Christopher John Mitchell, Everberg (GB); Douglas Hyndman Stewart, Stockton-on-Tees (GB)

(73) Assignee: Huntsman International LLC, The Woodlands, TX (US)

( * ) Notice: Subject to any disclaimer, the term of this patent is extended or adjusted under 35 U.S.C. 154(b) by 318 days.

(21) Appl. No.: 13/583,941

(22) PCT Filed: Mar. 18, 2010

(86) PCT No.: PCT/EP2010/053529
§ 371 (c)(1),
(2), (4) Date: Sep. 11, 2012

(87) PCT Pub. No.: WO2011/113491
PCT Pub. Date: Sep. 22, 2011

(65) Prior Publication Data
US 2013/0006018 A1    Jan. 3, 2013

(51) Int. Cl.
*C07C 209/36*    (2006.01)
(52) U.S. Cl.
CPC .................................. *C07C 209/36* (2013.01)
(58) Field of Classification Search
None
See application file for complete search history.

(56) References Cited

U.S. PATENT DOCUMENTS

| 2,458,214 A | 1/1949 | Souders |
| 4,288,640 A | 9/1981 | Schuster et al. |
| 6,040,481 A | 3/2000 | Chambost et al. |
| 6,479,704 B1 | 11/2002 | Nordquist et al. |
| 2008/0234518 A1 | 9/2008 | Sommer et al. |

FOREIGN PATENT DOCUMENTS

| EP | A 1882681 | 1/2008 |
| GB | A 508024 | 1/1948 |

OTHER PUBLICATIONS

RD-508024, Anonymous, "Manufacture of Aniline by the Hydrogenation of MonoNitrobenzene in a trickle bed reactor" Research Disclosure, Aug. 2006.

*Primary Examiner* — Clinton Brooks
(74) *Attorney, Agent, or Firm* — Huntsman International LLC

(57) ABSTRACT

A process for hydrogenating an aromatic nitro compound according to the invention comprises
  providing a hydrogen gas stream and a liquid aromatic nitro compound stream;
  providing a fixed bed catalytic reactor having an inflow side and an outflow side;
  feeding to the inflow side, the hydrogen gas stream and the liquid aromatic nitro compound stream;
  converting the hydrogen gas and the aromatic nitro compound into an aromatic amine, thereby providing a reactor effluent comprising the aromatic amine and water;
  evacuating the reactor effluent from the reactor at the outflow side of the reactor;
wherein an inert solvent or water is fed to the inflow side of the reactor at a molar ratio of moles inert solvent or water to moles hydrogen is more than 1.

10 Claims, 3 Drawing Sheets

PROCESS FOR THE CONVERSION OF AROMATIC NITRO COMPOUND INTO AMINES

CROSS-REFERENCE TO RELATED APPLICATIONS

Figure 1:
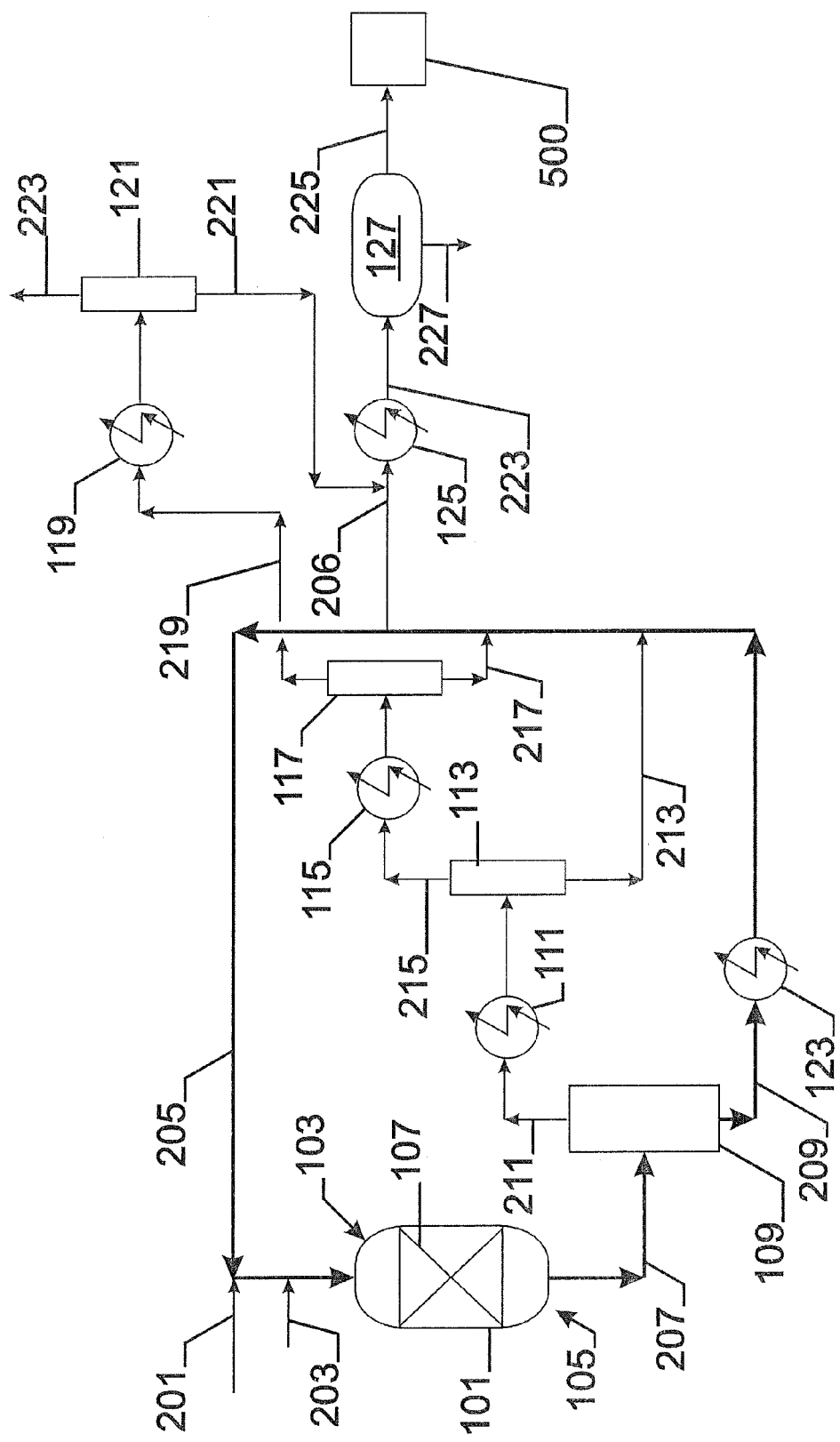

This application is the National Phase of International Application PCT/EP2010/053529 filed Mar. 18, 2010 which designated the U.S. The noted application is incorporated herein by reference.

The present invention relates to processes for conversion of aromatic nitro-compounds into aromatic amines, such as nitrobenzene into aniline. The invention further relates to the aromatic amines, such as aniline, obtainable and obtained by these processes.

Processes for hydrogenating an aromatic nitro compound, thereby providing a corresponding amine are well known. Such processes typically comprise
  providing a hydrogen gas stream and a liquid aromatic nitro compound stream;
  providing a fixed bed catalytic reactor having an inflow side and an outflow side;
  providing to said inflow side, said hydrogen gas stream and said liquid aromatic nitro compound stream;
  reacting said hydrogen gas and said aromatic nitro compound providing a reactor effluent comprising the corresponding aromatic amine and water;
  evacuating the reactor effluent from the reactor at the outflow side of said reactor.

It is an object of the present invention to reduce the amount of byproducts in the hydrogenated aromatic nitro-compound, i.e. the corresponding aromatic amine, in the reactor effluent, said byproducts being compounds having hydrogenated rings originating from the aromatic rings in the nitro-compound. The process according to the present invention may have an economically viable yield of conversion of aromatic nitro-compound into the corresponding aromatic amine.

The above objective is accomplished by processes according to the present invention.

According to a first aspect of the present invention, a process for hydrogenating an aromatic nitro compound is provided, the process comprises the steps of
  providing a hydrogen gas stream and a liquid aromatic nitro compound stream;
  providing a fixed bed catalytic reactor having an inflow side and an outflow side;
  feeding to said inflow side, said hydrogen gas stream and said liquid aromatic nitro compound stream;
  converting said hydrogen gas and said aromatic nitro compound into an aromatic amine, thereby providing a reactor effluent comprising water and said aromatic amine;
  evacuating said reactor effluent from the reactor at the outflow side of said reactor.

An inert solvent or water is fed to the inflow side of the reactor such that the molar ratio of moles inert solvent or water to moles hydrogen is more than 1.

The resulting hydrogenated aromatic nitro compound is an aromatic primary amine compound, the primary amine(s) resulting from the hydrogenation of the nitro group(s).

According to some embodiments, the molar ratio of moles inert solvent or water to moles hydrogen may be in the range of 1.5 to 7.5.

More preferred, the molar ratio of moles inert solvent or water to moles hydrogen may be in the range of 2 to 5, such as 2 to 4, e.g. 3.

The process according to the invention results in the provision of a reactor effluent, also referred to as reaction mixture, comprising an aromatic primary amine compound and water, together with a reduced amount of by-products having groups resulting from hydrogenation of the aromatic groups. The process can be run providing an industrially acceptable production yield.

Without wishing to be bound by any theory, in case an inert solvent or water is fed to the inflow side of the reactor at a molar ratio of moles inert solvent or moles water to moles hydrogen of more than one, and preferably in the ranges set out above, it is believed that this feeding of inert solvent or water influences the hydrogen partial pressure difference between the inflow side and the outflow side, the hydrogen partial pressure at the inflow side being higher than the hydrogen partial pressure at the outflow side. It is believed this effect, in particular using the ratio in the preferred ranges, results in the effect of reduced over-hydrogenated impurities in the effluent of the reactor. Feeding too much inert solvent or water may on the other hand effect a loss in amine output, i.e. a reduced conversions yield and may cause a drop in catalyst efficiency.

The term "partial pressure" of a gas or vapor is well known in the art. It means, for a gas or vapor present in a real or imaginary volume at a given temperature, the pressure which said gas or vapour would have if it alone would occupy this volume at this temperature.

In the context of this invention, the partial pressure of hydrogen, i.e. the hydrogen partial pressure, at a point in the reactor refers to the pressure which said hydrogen would have at an infinitesimal volume encompassing that point in the reactor, if the hydrogen alone would occupy this infinitesimal volume at the temperature present at that point.

In the hydrogenation process according to the invention, an excess of hydrogen is typically used. The molar ratio of moles hydrogen ($H_2$) to "A" times the moles of the aromatic nitro compound, "A" being three times the number of nitro groups per molecule of the aromatic nitro compound, is preferably ranging from 3.15 to 3.6. In other words, the hydrogen feed is preferably run in the range with 5 to 30% mole above the stochiometrical requirement to react all the nitro groups into primary amine groups. Varying the hydrogen feed can help to further control the molar ratio of moles water or inert solvent to moles of hydrogen.

Without wishing to be bound by any theory, it is believed that the higher hydrogen partial pressure at the inflow side of the reactor, where the hydrogen and the aromatic nitro compound, e.g. nitrobenzene are brought into contact, causes the hydrogenation reaction to take off quickly, initiating a high conversion of the nitro groups to primary amine groups, e.g. conversion of nitrobenzene to aniline, whereas the lower hydrogen partial pressure at the outflow side of the reactor decreases the formation of said by-products.

By careful control of the water or inert solvent feed at the inflow side of the reactor, a selectivity of nitro groups (in the feed) to amines (in the reactor effluent), e.g. selectivity of nitrobenzene to aniline, of 99.8% can be achieved, with a conversion rate of nitro groups, e.g. nitrobenzene, of 99.998%.

Conversion rate is the rate of moles of any converted aromatic nitro compound over rate of mols of aromatic nitro compound fed, expressed as percentage.

Selectivity is the rate of moles of the targeted amine product in the reactor effluent over the rate of moles aromatic nitro compound fed, expressed as a percentage.

There may remain a potential for incomplete reaction of the aromatic nitro compound, e.g. nitrobenzene, as it passes through the fixed bed reactor, due to e.g. channeling of either gas or liquid or both. Under such circumstances the concentration of aromatic nitro compound, e.g. nitrobenzene, exiting the catalyst bed may reach several thousand ppm aromatic nitro compound, e.g. nitrobenzene. This residual aromatic nitro compound, e.g. nitrobenzene, can be efficiently removed from the amine product, e.g. aniline product, by use of an in-line polishing device. This polisher takes the amine product, e.g. aniline product, at 200 to 230 deg C. and 30 to 40 barg from the exit of the reactor cooler. Hydrogen may be added to this polisher to aid conversion. The polisher may also use a catalyst of similar composition to the catalyst in the main, fixed bed reactor for hydrogenating the aromatic nitro compound. A residence time of 30 seconds to 2 minutes is suitable for conversion of the residual aromatic nitro compound, e.g. nitrobenzene.

To reduce or even avoid channeling of gas, liquid or both in the main reactor, it is possible to split the bed of the fixed bed reactor into several bed sections, where the gas and liquid from each bed is redistributed. This can be done using a mechanical redistribution device such as a bubble cap tray, or simple pipe risers.

By controlling the amount of inert solvent or water, optionally recycled water from the reactor effluent, being fed at the inflow side of the reactor, together with the aromatic nitro compound and the hydrogen, in the specified molar range, the hydrogen partial pressure may be controlled. Water or solvent gradually will evaporate during its passing through the reactor, and as such gradually increases its contribution to the pressure throughout the reactor, thereby possibly reducing but at least influencing the partial pressure of the hydrogen.

Additionally, the hydrogen partial pressure difference may be kept and controlled to a further extent by setting and optionally adjusting a temperature profile through the reactor. Preferably, at the inflow side and the region immediately following the inflow side, a temperature in the range of 160 degrees C. and 200 degrees C. is provided. Preferably, at the outflow side and the region immediately preceding the outflow side, a temperature in the range of 240 deg C. to 280 deg C. is provided. Hence preferably a temperature difference between 40 degrees C. and 100 degrees C. is provided over the reactor. The pressure at the inflow side, the outflow side and throughout the reactor may be kept substantially constant, and preferably within the range of 30 to 40 barg. The pressure drop between inflow and outflow may be 0.2 to 4 barg.

The term "barg" is understood as the pressure, expressed in bar, above atmospheric pressure.

Alternatively or additionally, the hydrogen partial pressure difference may further be controlled by setting and optionally adjusting the pressure or a pressure profile over the reactor.

The aromatic nitro compound may be nitrobenzene, nitro toluene, 2-nitro m-xylene, 4-nitro m-xylene, nitronaphtalene or dinitrotoluene, or combinations thereof.

Preferably water is added, either as fresh water, as water obtained by extraction from e.g. the reactor effluent, or water as part of recycled reactor effluent itself. Preferably, water is provided to the inflow side of the reactor by recycling a stream of reactor effluent to the inflow side (optionally after degassing and partial removal of the aromatic amine component), such that the molar ratio of moles hydrogen and moles water is within the specified range. The water may be recuperated from the liquid reactor effluent and/or from the gaseous mixture after degassing of the reactor effluent.

In case inert solvent is used, the inert solvent may be a solvent which is in liquid phase at the inflow side of the reactor under the process conditions at the inflow side, but which evaporates, partially or completely, during transfer through the reactor. The inert solvent may be recuperated from the liquid reactor effluent and/or from the gaseous mixture after degassing of the reactor effluent.

According to some embodiments, the aromatic nitro compound may be dinitrotoluene. According to some embodiments, the aromatic nitro compound may be nitrobenzene.

Preferably aniline is provided by the process according to the first aspect of the present invention, by hydrogenation of nitrobenzene with hydrogen.

This aniline may be used to provide methylenedianiline (MDA) by reacting said aniline with formaldehyde over a suitable catalyst, typically HCl. This MDA may then be used to provide methylene diphenyl diisocyanate (MDI) by converting the two amine groups into isocyanate groups, typically by reaction of the MDA with phosgene. This MDA may be used to provide Bis(aminocyclohexyl)methanes such as Bis(4-aminocyclohexyl)methane (H12MDI) by first hydrogenating said MDA with hydrogen to $H_{12}$MDA, and thereafter converting the two amine groups to isocyanate groups, typically by reaction of the $H_{12}$MDA with phosgene.

According to some embodiments, part of the reactor effluent may be recycled to the inflow side of the reactor.

According to some embodiments, at least part of the water from the reactor effluent may be recycled to the inflow side of the reactor.

Before recycling part of the water or the inert solvent from the reactor effluent, the water or inert solvent may be separated by generally known methods (such as e.g. liquid-liquid phase separation, gravitational and/or centrifugal liquid-liquid phase separation), from the reactor effluent.

In case water is used to control the molar ratio of water to hydrogen, the process hence may comprise the separation of the reactor effluent in an organic stream and an aqueous stream, the aqueous stream comprising the majority of the water from the reactor effluent, and thereafter recycling at least part of the aqueous stream to the inflow side for the reactor.

Additionally or alternatively, after the reactor effluent has left the reactor, the reactor effluent may be degassed, separating the hydrogen excess, aniline and the water vapor from a liquid reactor effluent comprising water and aniline. The water vapor may be condensed and partially or completely recycled to the inflow side of the reactor.

In a preferred set-up, the reactor effluent is separated in a vapor phase and a liquid phase.

The output of the fixed bed reactor is typically a liquid product and a gaseous product. Optionally, the liquid and gas product from the reactor are cooled/condensed separately. The gas product, which has a higher concentration of light impurities, and a lower concentration of heavy impurities than the total reactor product (i.e. the combination of gaseous and liquid reaction product), can become the principal reactor product, used as product for further processing. The obtained hydrogenated aromatic nitro compound may further be subjected to purification processes.

Some part of the liquid phase may be purged to evacuate the impurities from the process, whereas another part of the liquid phase can be used to recycle to the inflow of the reactor, being the source of water added to the reactor inflow according to the invention. Optionally, a part of the liquid phase may be used to evacuate less pure hydrogenated aromatic nitro compound from the process.

Such a mode of operation is favorable when a reactor is producing low concentrations of light impurities, and higher concentrations of heavy impurities.

The heavy impurities are preferably removed from the reactor system via a purge on the reactor recycle line which is typically 0.1 to 0.3 times the flowrate of the product. Operating in this mode has an added advantage with respect to nitrobenzene conversion: The condensed gas phase of the reaction is found to contain far lower concentrations of nitrobenzene than the liquid reactor product. This condensed gas phase can be used as final product and the unreacted nitrobenzene will principally be recycled back into the reactor and given another opportunity to react, although some nitrobenzene will escape via the purge flow. The amount escaping will be dependent on the purge rate. The overall net result is higher conversion of the nitrobenzene product to aniline.

Also the recovered hydrogen may be recycled to the inflow side of the reactor, e.g. by adding this recycled hydrogen to the fresh hydrogen stream prior to or at the inflow point of the hydrogen.

The recycle of the water or inert solvent from the reactor effluent, optionally by recycling a part of the reactor effluent, may be done by adding this recycled water or inert solvent to the liquid aromatic nitro compound stream.

Preferably the reactor is operated adiabatically and at a pressure equal throughout the reactor.

The hydrogenation is done using a catalyst to catalyze the hydrogenation reaction. Suitable catalysts may comprise metals from group VIII of the Periodic Table of the Elements (such as nickel, platinum or palladium) e.g. palladium supported on an alumina support. The catalyst may optionally comprise minor amounts of iron, lead, vanadium, platinum, barium or other metals. These additional elements may, all together typically provide less than 5% wt, based on the total weight of the total catalyst.

The catalyst may be carried by a catalyst carrier, such as alumina, silica, titanium dioxide or other carrier. The carrier is typically in the form of rods or spheres or any other geometrical shape. e.g. 1/16th to 1/8th diameter inch spheres. Alternatively, the catalyst can be provided in the form of extrudates, available in a plurality of shapes, e.g. cylinders, trilobes, quadrilobes and alike.

A typical volumetric flowrate of feed to volume of catalyst may be in the range of 0.2 to 2 $hr^{-1}$, preferably in the range of 0.5 to 1.5 $hr^{-1}$.

As all the reactants are fed at the inflow side of the reactor the streams of products in the reactor is co-current. This means that the streams, be it liquid or gas, flow through the reactor in the same direction from the inflow side to the outflow side.

The fixed bed reactor is preferably a trickle bed reactor. The reactor may be run adiabatically. The flow in the reactor may be in vertical direction, the inflow side and the outflow side being located substantially one above the other. Most preferred, a top-bottom flow is used, where the inflow side is located above the outflow side. A bottom-up flow, where the inflow side is located under the outflow side, is also possible. To control the hydrogen partial pressure better to a further extent, the reactor may be provided with cooling equipment such as e.g. shell and tube, plate and/or spiral heat exchanger systems.

According to a second aspect of the present invention, a mixture of an aromatic primary amine compound and water is provided, the mixture being obtained by a process according to the first aspect of the present invention.

According to a third aspect of the present invention, a mixture of an aromatic primary amine compound and water, obtainable by a process according to the first aspect of the present invention, is provided, the mixture further comprises less than 7500 ppm of compounds having groups resulting from hydrogenation of the aromatic groups of the aromatic primary amine compound.

Preferably the compounds having groups resulting from hydrogenation of the aromatic groups of the aromatic primary amine compound are present in an amount of less than 5000 ppm, such as in the range of 100 ppm to 5000 ppm.

In the above the ppm refers to the total weight of the component over the total weight of the mixture.

The mixture obtainable or obtained according to the present invention, has the advantage that it does not require further purification of the mixture prior to using the mixture in a process for producing isocyanates.

In particular, in case the aromatic primary amine compound is aniline, no purification of the mixture is required when the mixture is used to convert the aniline into methyl diphenyl diamine (MDA), which in its turn is a precursor in the production of methyl diphenyl diisocyanate (MDI).

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 2:
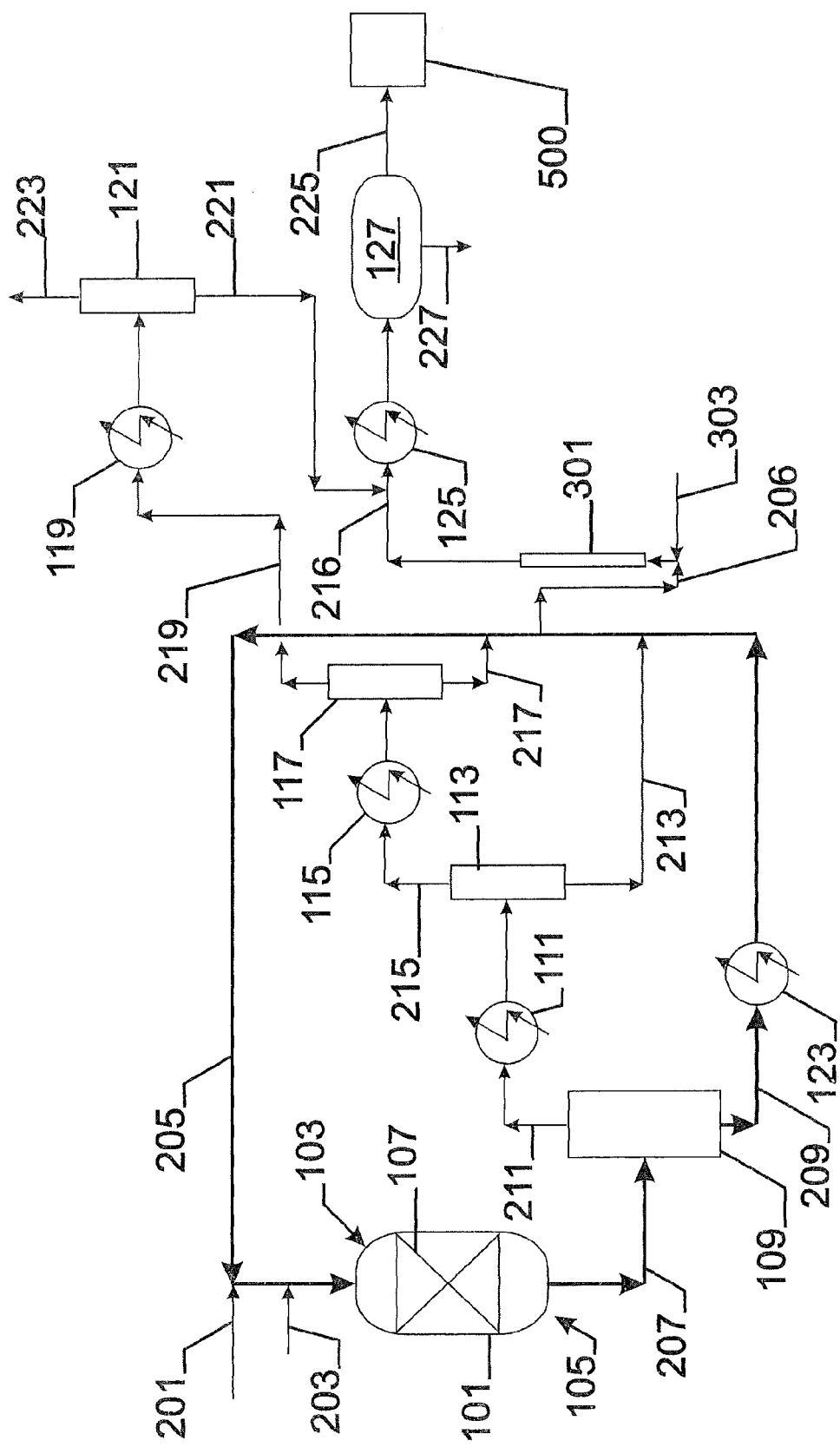
Figure 3:
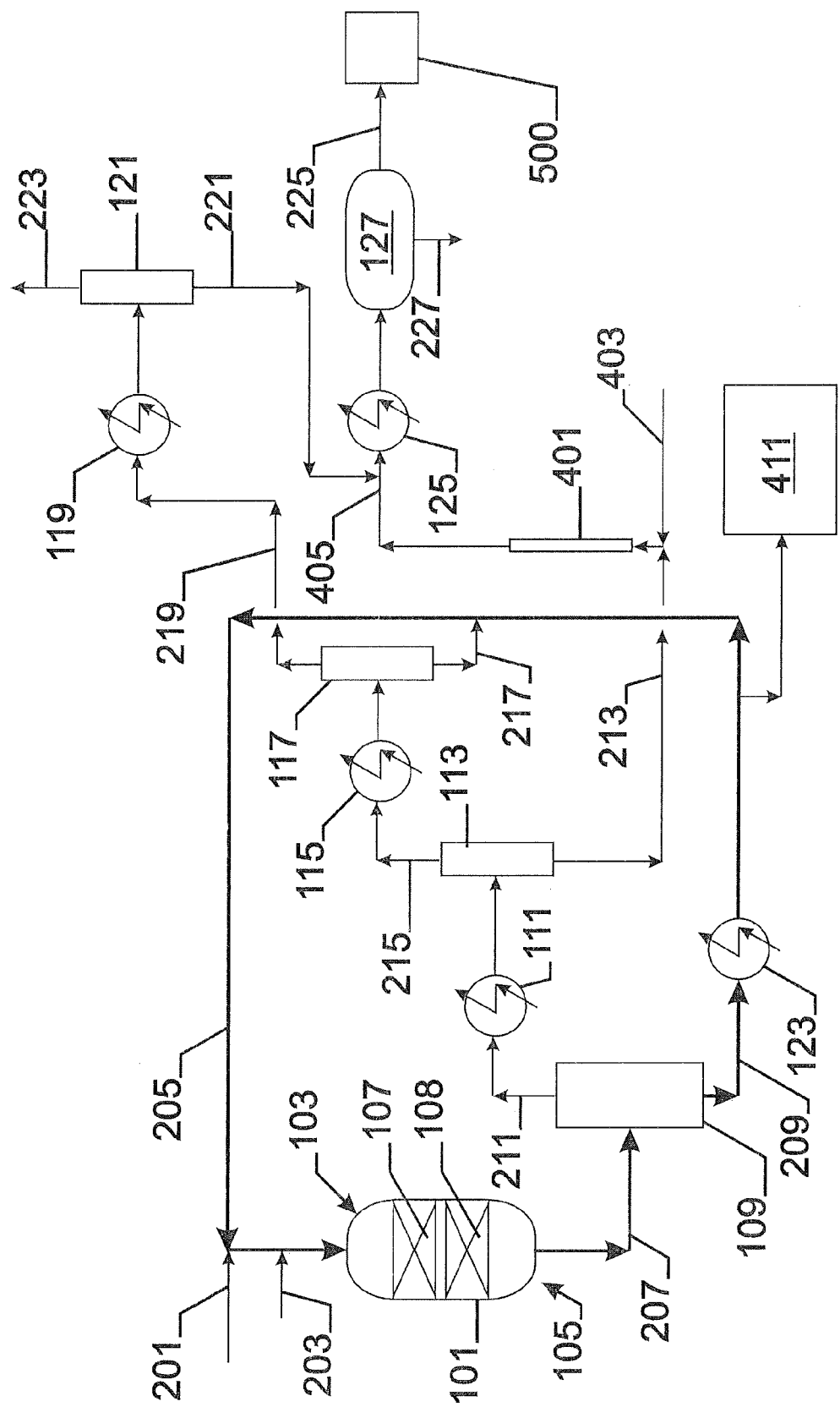

FIGS. 1, 2 and 3 are schematically views of processes according to the present invention.

The same reference signs refer to the same, similar or analogous elements in the different figures.

The present invention will be described with respect to particular embodiments. It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention: Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

The principle of the invention is hereinafter disclosed by means of various tests, run using various molar ratios $H_2O/H_2$ in the inflow of a "nitrobenzene to aniline" trickle bed reactor.

Using the reactor with feeds and settings as shown in table I, water was fed at various ratios compared to the hydrogen in the inflow. Two different catalysts were tested. The first catalyst (cat I) is an iron promoted palladium catalyst on an alumina support (1/16th inch spheres). The second catalyst (cat II) is a palladium on alumina hydrogenation catalyst commercially available from Johnson Matthey (Type 310/2 E 1.2 mm Hydrogenation Catalyst).

TABLE I

| test | 1 | 2 | 3 | 4 | 5 | 6 |
|---|---|---|---|---|---|---|
| Catalyst | I | I | I | I | II | II |
| $H_2$ feed (mol/h) | 0.277 | 0.277 | 0.277 | 0.277 | 0.277 | 0.277 |
| Nitrobenzene (mol/h) | 0.072 | 0.072 | 0.072 | 0.072 | 0.072 | 0.072 |
| Aniline (mol/h) | 0.582 | 0.582 | 0.582 | 0.582 | 0.582 | 0.582 |
| Water (mol/h) | 1.667 | 0.833 | 0.417 | 0 | 1.667 | 0 |
| Mol ratio $H_2O/H_2$ | 6 | 3 | 1.5 | 0 | 6 | 0 |
| Set point Temperature (deg C.) | 250 | 250 | 250 | 250 | 250 | 250 |
| Pressure (bar g) | 20 | 20 | 20 | 20 | 20 | 20 |
| Mass of catalyst, (g) | 4.0 | 4.0 | 4.0 | 4.0 | 4.0 | 4.0 |

"Bar g" is the pressure in excess over the actual ambient pressure (bar gauge) expressed in Bar.

In the table II under, the amount of over-reduced species in the reactor effluent, as determined by means of gas chromatography, (such as benzene, cyclohexylamine, cyclohexanol, cyclohexanone, dicyclohexyl amine, cyclohexylideneaniline, N-cyclohexylaniline, and diphenylamine) is set out. It is clear that for decreasing molar ratio of water over hydrogen, increasing over-reduced species are found.

TABLE II

| | test | | | | | |
|---|---|---|---|---|---|---|
| Over-reduced (ppm) | 1 | 2 | 3 | 4 | 5 | 6 |
| Benzene | 80 | 86 | 79 | 98 | 68 | 40 |
| Cyclohexylamine | 22 | 149 | 235 | 1515 | 0 | 546 |
| Cyclohexanol | 58 | 123 | 253 | 1018 | 40 | 46 |
| Cyclohexanone | 952 | 2289 | 2968 | 3818 | 610 | 2772 |
| Dicyclohexylamine | 0 | 0 | 0 | 249 | 0 | 0 |
| Cyclohexylideneaniline | 101 | 436 | 1256 | 2428 | 0 | 761 |
| N-cyclohexyl aniline | 75 | 713 | 1800 | 11039 | 19 | 4583 |
| Diphenylamine | 135 | 316 | 484 | 704 | 124 | 441 |
| Total* (ppm) | 1423 | 4112 | 7075 | 20869 | 861 | 9189 |
| Mol ratio $H_2O/H_2$ | 6 | 3 | 1.5 | 0 | 6 | 0 |

An industrial process set-up according to the present invention is schematically shown in FIG. 1. The process describes, as an example, a process for conversion of nitrobenzene to aniline. The process equipment comprises a fixed bed, trickle bed reactor 101 having an inflow side 103 and an outflow side 105, the inflow side 103 being located above the outflow side 105.

At the inflow side, a liquid nitrobenzene stream 201 and a gaseous hydrogen stream 203 is provided. To the nitrobenzene stream 201, a recycle stream 205 comprising water is added.

The reactor 101, comprising a fixed bed 107 of palladium containing catalyst, converts the nitrobenzene and hydrogen, flowing concurrent top-bottom through the reactor 101, into aniline. The fixed bed 107 may comprise only one or a number of consecutive beds of catalyst. At the inflow side 103, a temperature of about 160 degrees C. to 210 degrees C. and a pressure of about 25 barg to 45 barg is set. At the outflow side 105 a temperature of about 240 degrees C. to 280 degrees C. and a pressure of about 21 to 45 barg is set. The reactor effluent 207 leaves the reactor 101 at the outflow side 105. The reactor effluent 207 is separated into a first gaseous stream 211 and a first liquid stream 209 by means of a first phase separator 109. The first gaseous stream 211, cooled by cooling means 111, is again phase separated by means of a phase separator 113 in a second gaseous stream 215 and a second liquid stream 213. The second gaseous stream 215, cooled by cooling means 115, is again phase separated by means of a phase separator 117 in a third gaseous stream 219 and a third liquid stream 217. The third gaseous stream 219 is further cooled by a cooling means 119, and once again the liquid phase after cooling is provided as a liquid stream 221 by separation this liquid phase from the vent hydrogen 223 using a separator 121.

The liquid streams 209 (after being cooled by means of a cooling means 123), 213 and 217, are combined and split in a recycle stream 205 and a liquid stream 206 for further processing. Liquid streams 206 and 221 are combined and further cooled by cooling means 125. The cooled liquid reaction product 223 is provided in a liquid-liquid phase separating means 127, where the aniline 225 is separated from the aqueous effluent 227. The aniline may be subject of further purification 500.

This process runs the reactor 101 adiabatically.

The feed-back rate of the reactor effluent, by means of liquid stream 205 and the hydrogen gaseous feed stream 203 are such that at the inflow side, the molar ratio of water over hydrogen (the water being present in recycle stream 205) is in the range of 2 to 4, such as 3. Feed-rate hydrogen is fed at a stochiometrical excess of 20% to 25% over nitrobenzene.

Tests have shown that by varying the molar ratio water to hydrogen a the inflow side between 1.8 and 7, the composition of the reactor effluent 207 leaving the reactor 101 may comprise less than 7500 ppm over-hydrogenated nitrobenzene species, whereas the yield of aniline is acceptable.

A second process according to the present invention is shown schematically in FIG. 2. Same reference numbers refer to the same features as explained for FIG. 1. The process further comprises a polisher 301. After providing the liquid stream 206 for further processing, the liquid stream 206 is fed to the polisher 301 with the addition of a minor amount of gaseous hydrogen 303. The polisher converts a major part of the nitrobenzene in stream 206 into aniline. A polished liquid stream 216 is provided. Liquid streams 216 and 221 are combined and further processed as in process subject of FIG. 1.

A third process according to the present invention is shown schematically in FIG. 3. Same reference numbers refer to the same features as explained for FIG. 1.

The fixed bed reactor 101 is provided with two subsequent fixed beds 107 and 108 of catalyst. From the first liquid stream 209, a minor stream 411, is taken of for purging 412 and evacuation of heavy contaminants.

The remaining part of the first liquid stream 209, after cooling and taking out the part 301, is combined with third liquid stream 217 and recycled to the inlet side 103 of reactor 101 as recycled stream 205.

The second liquid stream 213 is fed to the polisher 401 with the addition of a minor amount of gaseous hydrogen

403. The polisher converts a major part of the nitrobenzene in stream 213 into aniline. A polished liquid stream 405 is provided. Liquid streams 405 and 221 are combined and further processed as in process subject of FIG. 1.

It is to be understood that although preferred embodiments and/or materials have been discussed for providing embodiments according to the present invention, various modifications or changes may be made without departing from the scope and spirit of this invention.

The invention claimed is:

1. A process for hydrogenating an aromatic nitro compound, the process comprising:
   providing a hydrogen gas stream and a liquid aromatic nitro compound stream;
   providing a fixed bed catalytic reactor having an inflow side and an outflow side;
   feeding to said inflow side, said hydrogen gas stream and said liquid aromatic nitro compound stream;
   converting said hydrogen gas and said aromatic nitro compound into an aromatic amine, thereby providing a reactor effluent comprising said aromatic amine and water; and
   evacuating said reactor effluent from the reactor at the outflow side of said reactor;
   wherein an inert solvent or water is fed to the inflow side of the reactor at a molar ratio of moles inert solvent or water to moles hydrogen is in a range of about 1.5 to 7.5 and wherein the pressure at the inflow side, the outflow side and throughout the reactor is kept within a range of 30 to 40 barg and the pressure drop between the inflow side and outflow side of the reactor is 0.2 to 4 barg and the aromatic nitro compound is nitrobenzene and the aromatic amine is aniline.

2. The process for hydrogenating an aromatic nitro compound according to claim 1, wherein a part of the reactor effluent is recycled to the inflow side of the reactor.

3. The process for hydrogenating an aromatic nitro compound according to claim 1, wherein at least part of the water from the reactor effluent is recycled to the inflow side of the reactor.

4. A process for hydrogenating an aromatic nitro compound, comprising:
   feeding a hydrogen gas stream, a liquid aromatic nitro compound stream and an inert solvent or water to an inflow side of a fixed bed catalytic reactor, wherein the inert solvent or water is fed to the inflow side of the reactor at a molar ratio of moles inert solvent or water to moles hydrogen in a range of about 1.5 to 7.5 and wherein the pressure at the inflow side, the outflow side and throughout the reactor is kept within a range of 30 to 40 barg and the pressure drop between the inflow side and outflow side of the reactor is 0.2 to 4 barg; and
   converting the hydrogen gas and the aromatic nitro compound into an aromatic amine wherein the aromatic nitro compound is nitrobenzene and the aromatic amine is aniline.

5. The process of claim 4, further comprising forming an effluent in the fixed bed catalytic reactor and evacuating the effluent out of the fixed bed catalytic reactor at an outflow side of the fixed bed catalytic reactor, wherein the effluent includes the aromatic amine and water, and wherein a part of the effluent is recycled to the inflow side of the fixed bed catalytic reactor.

6. The process of claim 5, wherein at least part of the water from the effluent is recycled to the inflow side of the fixed bed catalytic reactor.

7. The process of claim 5, wherein a hydrogen partial pressure at the inflow side is maintained to be higher than a hydrogen partial pressure at the outflow side.

8. A process for hydrogenating an aromatic nitro compound, comprising:
   feeding a hydrogen gas stream, a liquid aromatic nitro compound stream and an inert solvent or water to an inflow side of a fixed bed catalytic reactor wherein a molar ratio of the inert solvent or water to the hydrogen gas is in a range of about 1.8 to 7 and wherein the pressure at the inflow side, the outflow side and throughout the reactor is kept within a range of 30 to 40 barg and the pressure drop between the inflow side and outflow side of the reactor is 0.2 to 4 barg;
   converting the hydrogen gas and the aromatic nitro compound into an aromatic amine;
   forming an effluent in the fixed bed catalytic reactor, wherein the effluent includes the aromatic amine and water; and
   evacuating the effluent out of the fixed bed catalytic reactor at an outflow side of the fixed bed catalytic reactor, wherein the effluent contains less than 7500 ppm of over-hydrogenated impurities wherein the aromatic nitro compound is nitrobenzene and the aromatic amine is aniline.

9. The process of claim 8, wherein a part of the effluent is recycled to the inflow side of the fixed bed catalytic reactor.

10. The process of claim 9, wherein at least part of the water from the effluent is recycled to the inflow side of the fixed bed catalytic reactor.

* * * * *